United States Patent [19]

Durbin et al.

[11] Patent Number: 4,874,706

[45] Date of Patent: Oct. 17, 1989

[54] MANUFACTURE AND USE OF TAGETITOXIN

[75] Inventors: Richard D. Durbin, Cross Plains, Wis.; Jean H. Lukens, Cambridge, Mass.; Thomas F. Uchytil; Nicholas Rhodehamel, both of Madison, Wis.

[73] Assignee: Wisconsin Alumni Research Foundation, Madison, Wis.

[21] Appl. No.: 15,174

[22] Filed: Feb. 17, 1987

Related U.S. Application Data

[63] Continuation-in-part of Ser. No. 906,486, Sep. 10, 1986, abandoned.

[51] Int. Cl.[4] ................................................ C12R 1/38

[52] U.S. Cl. ..................................... 435/253.3; 47/58; 71/87; 71/90; 435/84; 435/105; 435/117; 435/130; 435/137; 435/874

[58] Field of Search ................. 435/84, 105, 117, 130, 435/137, 253.3, 874; 47/58; 71/87, 90

[56] References Cited

PUBLICATIONS

Mitchell et al., "Tagetitoxin, a Toxin Produced by Pseudomonas Syringae pv. tagetis: Purification and Partial Characterization," Physiol. Plant Pathol. (1981) 18, 157-168.

Lukens et al., "Tagetitoxin Affects Plastid Development in Seedling Leaves of Wheat," Planta (1985) 165: 311-321.

Hellmers, "Bacterial Leaf Spot of African Marigold (Tagetes erecta) caused by *Pseudomonas tagetis* sp. n.," Acta Agri. Scand. 5: 185-200 (1955).

Jutte and Durbin, "Ultrastructural Effects in Zinnia Leaves of a Chlorosis-Inducing Toxin from *Pseudomonas tagetis*," Phytopathology 69(8): 839-842 (1979).

Mitchell and Hart, "The Structure of Tagetitoxin, a Phytotoxin or *Pseudomonas syringae pv. tagetis*," *Phytochemistry*, 22(6): 1425-1428 (1983).

Rhodehamel, "Host Range of Strains of *Pseudomonas syringae* pv. *tagetis*," Plant Disease 69(7): 589-591 (1985).

Styer and Durbin, "Isolation of *Pseudomonas syringae* pv. *tagetis* from Sunflower in Wisconsin," *Plant Disease* 66: 601 (1982).

Styer and Durbin, "Common Ragweed: a New Host or *Pseudomonas syringae* pv. *tagetis*," Plant Disease 66: 71 (1982).

Styer and Durbin, "Influence of Growth Stage and Cultivar on Symptom Expression in Marigold, Tagetes sp. Infected by *Pseudomonas syringae* pv. *tagetis*," *HortScience* 16(6): 768-769 (1981).

Styer et al., "Occurrence in the United States of a Marigold Leaf Spot Incited by *Pseudomonas tagetis*," Plant Disease 65: 101-102 (1980).

Trimboli et al., "Apical Chlorosis and Leaf Spot of Tagetes spp. Caused by *Pseudomonas tagetis* Hellmers," *Aust. J. Agric. Res. 29: 831-839 (1978).*

*Primary Examiner*—Robert A. Wax
*Attorney, Agent, or Firm*—Quarles & Brady

[57] ABSTRACT

An exotoxin of the plant pathogen, *Pseudomonas syringae* pv. *tagetis* selectively inhibits the development of chloroplasts in growing plant tissue. The exotoxin, known as tagetitoxin, can be produced efficiently from a mutant high-producing line of the bacteria, designated C42mr2+. The tagetitoxin can also be readily purified from the culture medium of the bacteria.

5 Claims, No Drawings

MANUFACTURE AND USE OF TAGETITOXIN

GOVERNMENT RIGHTS

This invention was made with U.S. Government support under the USDA Broad Form Cooperative Agreement awarded by the U.S. Department of Agriculture. The Government has certain rights in this invention.

CROSS-REFERENCE TO RELATED APPLICATION

This application is a continuation-in-part of application Ser. No. 906,486 filed Sept. 10, 1986 abandoned.

FIELD OF THE INVENTION

The present invention relates to toxins in general and relates, in particular, to the production and use of tagetitoxin.

BACKGROUND OF THE INVENTION

A disease of African marigolds, Tagetes erecta, was recognized in the 1930's in which the leaves of the plants were curled and abnormal and also densely covered by necrotic spots. In 1955, Danish plant pathologist Ernst Hellmers demonstrated that the disease was caused by a Pseudomonas bacterium, Acta Agric. Scand. 5:185-200 (1955). In investigating an outbreak of disease causing losses of marigold seedlings of Tagetes erecta in Australia characterized principally by apical chlorosis, cultures of Pseudomonas bacteria were again isolated. It was found in this case that cell-free culture filtrates of cultures of the pathogenic bacteria were also phytotoxic, indicating that the agency of pathogenesis of the bacteria was an exotoxin capable of blocking chloroplast development in growing plant tissue but which does not otherwise appear to effect existing chlorophyll in plants. Aust. J. Agric. Res. 29:831-839 (1978). The toxin produced by the bacteria, which is now referred to as Pseudomonas syringae pv. tagetis, has been referred to as tagetitoxin. Tagetitoxin has been demonstrated to be a low molecular weight heterocyclic organic compound. The structural data available for the compound suggests that it includes an eight membered ring, with a sulfur atom in the ring, and also includes an amino group and a phosphate group joined to points on the ring. Phytochemistry 22:1425-1428 (1983). The proposed structure of tagetitoxin is as follows:

SUMMARY OF THE INVENTION

The present invention is summarized in that a strain of Pseudomonas syringae pv. tagetis has been created which allows yield of tagetitoxin at a level ten-fold higher than previously obtainable. The present invention is also directed to a method of purifying tagetitoxin from a culture suspension of the bacterial strain. The present invention is also directed toward the use of tagetitoxin as a plant growth control agent.

Other objects, advantages and features of the present invention will become apparent from the following specification.

DESCRIPTION OF THE INVENTION

As described above, there has been prior investigation as to the mechanism of pathogenesis caused by the bacteria Pseudomonas syringae pv. tagetis, indicating that the method of toxic activity is through the toxin now referred to as tagetitoxin. While the chemical structure of tagetitoxin has been tentatively resolved, investigation into the manufacture and use of the toxin has been hampered by the difficulty in obtaining reasonable quantities of the toxin for larger scale tests. It will be demonstrated here how the toxin can be created in experimentally useful quantities through the use of a unique and novel high producing strain of bacteria, and through an efficient method of purifying the toxin from the strain in which it is produced. In addition, it will be demonstrated that the toxin has potential utility as a herbicide and may, in fact, have activity and utility in other areas if the chemical structure of the toxin itself can be slightly modified.

It had been previously demonstrated, as referred to above, that plants infected with P. syringae pv. tagetis developed apical chlorosis. The tissues which become chlorotic are usually morphologically normal, except for the failure to have proper chloroplast development. Interference by the tagetitoxin with chloroplast-specific metabolism has been demonstrated to be light independent. Additional research, not yet published, has suggested that the effect of the toxin is to interfere with RNA transcription in prokaryotic but not eukaryotic RNA transcriptional systems at physiological concentrations, i.e. in in vitro experiments the toxin inhibits transcriptional activity of prokaryotic, but not eukaryotic, systems at 1 micromolar. Both in vitro and in vivo experiments in plants demonstrate that the toxin inhibits the transcriptional activity necessary to create chloroplasts, but does not affect nuclear DNA activity or the transcriptional systems of mitochondrial genes.

In order to further investigate the activity and utility of tagetitoxin in various systems, it is necessary to create sufficient quantities of the toxin itself. Native strains of P. syringae pv. tagetis can, and have been, isolated from the wild from six plant hosts in the family Compositae. All of the strains isolated from the wild tend to be host specific, as far as bacterial pathogenesis, even though the toxin produced from any strain of bacteria is not host specific, but is widely phytotoxic. The toxin produced from any one strain can be assayed by means of a standard bioassay developed here. The zinnia bioassay disclosed here has been developed as a methodology to provide such a standard assay for toxin activity. Wild type bacterial strains produce toxin at a level such that a positive Zinnia bioassay is possible only at a dilution level of ten-fold or less.

It has been observed in culture that when subjected to stress antibiotic that some of the cultures of strains of this bacteria will mutate into a rare, aberrant colony type. The mutant colony type produces much more extra cellular polysaccharide than wild-type colonies, and produces roughly an order of magnitude more toxin in vitro than parent strains. This mutant colony type also has a mucoid appearance. The mucoid mutants are very rare but do occur with regularity. The mucoid colonies, in consecutive serial transfers, will spontaneously revert to a non-mucoid phenotypes losing, at the same time, the high-toxin production capability. The inventors here have discovered one instance in which a mucoid reversion failed to lose its high-toxin production capability. Since the mucoid strains are much more difficult to grow and work with, it was this revertant strain, which is non-mucoid and still high-toxin producing, which is useful to produce toxin in accordance with the present invention.

As will be demonstrated below, it has also been discovered that tagetitoxin can be demonstrated to have herbicidal effect on emerging seedlings. This herbicidal activity occurs because of the chlorotic effect that the toxin has upon growing plant tissues. Young seedlings treated with tagetitoxin will emerge and continue to grow, although they will be chlorotic, until seed storage saccharide reserves are depleted. It has been found that tagetitoxin does not visually affect the existing chloroplasts in plant tissues into which it is introduced, but only interferes with the creation and fabrication of new chloroplasts. Accordingly, emergence stage application would probably be recommended for the toxin to have a herbicidal effect in the field.

EXPERIMENTAL EXAMPLES

Creation and Identification of High Toxin Producing Strain

A strain of *Pseudomonas syringae* pv. tagetis was originally isolated from marigold cultivars in Australia by Trimboli and his co-workers. This wild-type strain was supplied to the inventors here in late 1977. The original strain has been maintained in 0.85% saline solution at 4° at all times since. Colonies grown out from this strain produced tagetitoxin in vitro at a level similar to that produced by wild-type strains isolated from marigolds and other plant varieties. This level of tagetitoxin production allows for a ten-fold dilution in the tagetitoxin resultant from the production process described herein while still yielding a positive Zinnia bioassay result.

Single pv. tagetis cells were isolated from the culture of the Australian strain. Those cells were then grown out in culture and selected for antibiotic resistance. The cultures produced were serially introduced to increasing levels of rifampicin and streptomycin up to levels of 200 micrograms per milliliter. The parent Australian strain is sensitive to both these antibiotics at this level. One of the single-cell lines derived from this procedure was antibiotic resistant, and was designated C42. In the process of experimental handling of C42, it was observed that one rare, abberant colony type appeared in the serially reproduced colonies of this strain. The colony-type was mucoid in appearance and produced much more extracellular polysaccharide than other non-mucoid colony types of this strain. The mucoid colony types also produced roughly an order of magnitude more tagetitoxin in vitro as measured by the Zinnia bioassay. The mucoid colony types were designated C42m.

Subsequent to isolating C42m, another single mucoid colony was observed and isolated from a ragweed pv. tagetis strain after similar selection for resistance to rifampicin and streptomycin. This mucoid colony type behaves similarly in culture to C42m. The mutation to this phenotype is also rare in colonies isolated from ragweed. A screening effort which screened $3.75 \times 10^6$ colonies found no second mucoid colony. The fact that the mucoid strain is this rare, and the fact that the mucoid colony types have only been isolated from pv. tagetis strains which have had a forced resistance to antibiotics, suggest a possible relationship between the phenotype and the selection process for antibiotic resistance. There is no firm evidence as yet that this is the case, however.

It has been observed that from C42m, and also from the mucoid colony created from the ragweed strain, that non-mucoid colonies arise at a relatively high frequency, approximately one per thousand, in liquid culture. In consecutive serial transfers of the strains, the proportion of mucoid colonies in the culture decreases rapidly. With the loss of the mucoid phenotype, colonies also typically revert to low production of toxin. While studying the revertant non-mucoid colonies, a single colony was recognized and identified as C42mr2+. The "r" indicates that the colony was a revertant type. This colony was unusual among all revertant colonies in that it remained an in vitro producer with high-toxin production capability, producing roughly one order of magnitude more toxin than wild-strains. The "+" is intended to signify this high-producer phenotype. The characteristic has been found to be stable in this culture, and the level of toxin production remains the same even after three successive serial transfers in liquid culture of this strain.

A sample of C42mr2+ has been deposited with the American Type Culture Collection in Bethesda, Maryland and was accorded Accession Number 53534 on Sept. 8, 1986. This strain can be cultivated on any normal bacterial cultivation medium, though it prefers medium including glucose, such as Woolley's medium, at room temperature.

Zinnia Bioassay

The titre of tagetitoxin in liquids was measured by use of a bioassay developed for this purpose. The bioassay used nine to fourteen day old Zinnia seedlings of variety Polar Bear. The plants were grown in a controlled phytotron chamber at 28° C. with a twelve hour photo period. Illumination was provided by Sylvania Cool-White, VHO florescent tubes ($280.9+$or $-12.0$ $mEm_{-2}S_{-1}$). A quantity of Woolley's medium with 2% glucose as a carbon source was then inoculated with an inoculum of pv. tagetis and incubated on a rotary shaker at 250 rpms for six days. From the resulting culture, one milliliter was then harvested and sterilized in a 1.5 milliliter microfuge tube by the addition of 0.4 milliliters of chloroform and vortexing. The microfuge tube is then centrifuged for two minutes both to separate the aqueous and organic phases and to remove the cells from the culture broth.

The actual assay itself was performed by placing a 20 microliter droplet of the sterilized culture broth in the cotyledonary axil of the Zinnia seedling. A dissecting needle is used to puncture the stem beneath the droplet. The droplet was then normally drawn into the seedling by the transpirational stream.

The results of the assay can be read in thirty-six to forty-eight hours after treatment. Apical chlorosis was evident in plants treated with a positive control and was taken thereafter as positive evidence of tagetitoxin in the culture broth. All samples were tested on two plants. A negative control was used of chloroform-sterilized, distilled, deionized water, which caused no discernable effect on the Zinnia seedlings.

The relative titre of tagetitoxin in culture broth was determined by serial dilutions to the point of insensitivity in the assay. The sterilized culture broth was diluted 10 to 80 times at doubling intervals with sterile distilled, deionized water and tested in the Zinnia assay. The absolute amount of toxin required to give a minimally positive reading was 20 nanograms. This corresponds to a molar concentration of tagetitoxin of 2.3 micromolar. Therefore it was determined that a sample of unknown concentration which gave a positive reading after having been diluted ten times was 23 micromolar tagetitoxin.

Production of Tagetitoxin

For optimal production of tagetitoxin, the strain designated C42mr2+ of *Pseudomonas syringae* pv. tagetis is used. It has been found that this strain grows readily in a modified Woolley's medium.

The variant in Woolley's medium used successfully to grow this culture is composed as follows:

| Medium | |
|---|---|
| $KNO_3$ | 5 g |
| $K_2HPO_4.3H_2O$ | 1.05 g |
| $NaH_2PO_4.7H_2O$ | 1.34 g |
| $MgSO_4.7H_2O$ | .20 g |
| $CaCl_2.H_2O$ | .10 g |
| $FeSO_4.7H_2O$ | 20 mg |
| Glucose | 20 g |
| $H_2O$ (demineralized) | 1 L |

These ingredients, except for the glucose, were conventionally autoclaved for thirty minutes at 121° C. The glucose was conventionally sterilized separately and added to the autoclaved medium after the temperature was below 60° C.

One liter of the medium was then placed in 2.8 liter flasks and inoculated with 1 milliliter of an isolate of the culture C42mr2+ at a density of 4.00 at $OD_{500}$. The flasks were then immediately placed on a circular shaker rotating at 250 rpm at room temperature and incubated for four days.

The bacterial cells were removed from the culture medium by centrifugation in a JA-18 rotor at 15000 rpm for ten minutes at 4° C. The supernatant from the centrifugation was collected and 10 milliliters per liter of chloroform was added to sterilize the culture filtrate. The culture filtrate from each flask was then bioassayed using the dilution end point Zinnia bioassay. Normally with this system, the filtrate resulting from a culture could be diluted forty to fifty times while exhibiting demonstrable sensitivity in the Zinnia bioassay.

Tagetitoxin Purification

The following process describes a method used to purify the tagetitoxin from the culture filtrate obtained from the production methodology described above. The first step in the purification of the tagetitoxin was performed on an analytical grade ion-exchange column (50–100 mesh AG50W-X4 Bio-Rad column (32 centimeters by 2 centimeters)) in the H+ form. Culture filtrate was percolated through the column in aliquots of 500 milliliters followed by 100 milliliters of water wash. The pH of the effluent was maintained between 6.5 and 7.0 with 6 M sodium hydroxide. The column effluent was again tested in the Zinnia bioassay and delivered an end point dilution of between 40 and 50 times while retaining sensitivity in the assay.

The second step in the process of purifying the tagetitoxin consisted of passing the effluent again through an analytical grade ion-exchange column (50–100 mesh AG2-X8 Bio-Rad, column (32 centimeters by 2 centimeters)) converted from the chloride to the bicarbonate form by passing 500 milliliters of 0.5 molar ammonium bicarbonate through the column followed by 100 milliliter of water wash. To this column 500 milliliters of the effluent from the first step was then passed through again followed by 100 milliliter water wash. The toxin remains in the column and the column effluent was negative in the Zinnia bioassay. Subsequently 500 milliliters of 0.6 molar ammonium bicarbonate, 20% methanol and 1% tetrahydrofurin was used to elute the toxin from the column. The ammonium bicarbonate was removed in vacuo. The Zinnia bioassay was negative without dilution both, for the column effluent and for the water wash. The fraction removed from the resin was assayed and yielded an end point dilution still in the range of 40 to 50 dilutions while retaining sensitivity.

The dried toxin fraction was then treated with 15 milliliters of 30% methanol when allowed to stand for 2 hours at −10° C. The precipitate which formed was removed by centrifugation at 10,000 rpm for 10 minutes at 4° C. The precipitate was then washed once with 30% methanol which was added to the original supernatant. All of the activity remained in the suspension fraction.

The third step consisted of a chromatographic column (LH-20 (Pharmacia) column (81 centimeters×2 centimeters)) run on a ratio of methanol to water of 1 to 1. One milliliter (50 milliliter cultural filtrate equivalent) was applied to the column and 15 minute (4.5 milliliter) fractions were collected at a flow rate of 0.37 milliliters per minute. The Zinnia assay was positive for fractions 18 through 27. Usually fractions later than 23 to 25 were contaminated by traces of a pigment. The clear fractions were pooled separately from the pigmented fractions which were also pooled and re-run on an LH 20 column (55 centimeters by 20 centimeters using Milli Q $H_2O$ as the solvent and having a flow rate of 0.52 milliliters per minute. Again 15 minute (8.1 milliliter) fractions were collected and bioassayed. Fractions 10 to 13 were positive for toxin activity and free from the pigment. Positive fractions from the two LH-20 runs were bulked and re-run on LH-20 using water as a solvent.

The final preparation was stable when held in the dry state at −35° C. Within limits of the sensitivity of the bioassay, the overall recovery of toxin appeared to approach 100%.

Effect of Tagetitoxin on Seedlings

Seedlings of spring wheat (*Triticum aestivum* L. cv. Lathrop) were grown on filter paper at 22° C. in darkness or with twelve hour photoperiods under cool-white florescent lamps. Wheat seeds were germinated on filter paper disks kept moist with a solution containing between $10^{-4}$ to $10^{-8}$ molar tagetitoxin, or with distilled water, and the root systems of the seedlings were moistened with either distilled water or $5 \times 10^{-5}$ molar tagetitoxin. The seedlings were harvested between eight and ten days after germination when the first leaves were 8 to 12 centimeters long.

It was found that the tagetitoxin has little or no effect on the morphology, growth rate or fresh weight of developing wheat seedlings. The only visual effect of the seedlings which could be observed from the toxin treatment is on leaf pigmentation. The seedlings germinated and grown in this fashion completely lack chlorophyll, and were white or pale yellow. Examination of the ultrastructure of the leaves revealed that chloroplasts were not properly formed and lacked internal structure. It was thus concluded that the tagetitoxin has a specific mode of action effective on chloroplast development, but not on other cellular processes in plant cells.

We claim:

1. A biologically pure culture of a strain of *Pseudomonas syringae* pv. tagetis which has been mutated to produce tagetitoxin at a level at least ten fold higher than wild-type strain.

2. *Pseudomonas syringae* pv. tagetis of the strain C42mr2+, ATCC accession No. 53534.

3. A method of producing tagetitoxin comprising the steps of cultivating a strain of *Pseudomonas syringae* pv. tagetis which has been mutated to produce tagetitoxin at a level at least ten fold higher than wild-type strains, lysing the cells of the cultured bacteria, and recovering tagetitoxin from the culture suspension.

4. A method as claimed in claim 3 wherein the step of recovering the tagetitoxin includes the steps of centrifuging the culture suspension, isolating the supernatant, passing the supernatant through a reducing ion-exchange column, passing the effluent through an oxidizing ion exchange column, resolubilizing the fraction retained in the oxidizing ion exchange column, passing the recovered fraction through a chromatagraphic column, and recovering the fractions containing the tagetitoxin.

5. A method of controlling plant growth comprising applying to the plant a biologically effective amount of tagetitoxin sufficient to cause chlorosis in the plant tissues, the tagetitoxin produced by the method of claim 3.

* * * * *